United States Patent
Feuerhelm-Heidl

(10) Patent No.: US 10,352,949 B2
(45) Date of Patent: Jul. 16, 2019

(54) BIOMARKER AND METHODS FOR EARLY DIAGNOSIS OF ALZHEIMER'S DISEASE

(71) Applicant: predemtec GmbH, Hennigsdorf (DE)

(72) Inventor: Annegret Feuerhelm-Heidl, Hennigsdorf (DE)

(73) Assignee: PREDEMTEC AG, Allschwil (CH)

( * ) Notice: Subject to any disclaimer, the term of this patent is extended or adjusted under 35 U.S.C. 154(b) by 0 days.

(21) Appl. No.: 15/221,069

(22) Filed: Jul. 27, 2016

(65) Prior Publication Data

US 2016/0334422 A1    Nov. 17, 2016

Related U.S. Application Data

(63) Continuation-in-part of application No. PCT/EP2015/051677, filed on Jan. 28, 2015.

(60) Provisional application No. 61/932,307, filed on Jan. 28, 2014.

(30) Foreign Application Priority Data

Jan. 28, 2014  (EP) .................................... 14152770

(51) Int. Cl.
*G01N 33/53*   (2006.01)
*G01N 33/542*   (2006.01)
*G01N 33/566*   (2006.01)
*G01N 33/68*   (2006.01)

(52) U.S. Cl.
CPC ..... *G01N 33/6896* (2013.01); *G01N 2333/48* (2013.01); *G01N 2333/495* (2013.01); *G01N 2333/515* (2013.01); *G01N 2333/523* (2013.01); *G01N 2333/54* (2013.01); *G01N 2333/65* (2013.01); *G01N 2800/2821* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

| WO | 2005/017203 A1 | 2/2005 |
| WO | 2005/017203 A2 | 2/2005 |
| WO | 2005/05292 A2 | 6/2005 |
| WO | 2005/052592 A2 | 6/2005 |
| WO | 2006/036182 A2 | 4/2006 |
| WO | 2006/133423 A1 | 12/2006 |
| WO | 2009/149185 A2 | 12/2009 |
| WO | 2011/039366 A1 | 4/2011 |
| WO | 2011/063453 A1 | 6/2011 |
| WO | 2011/094535 A2 | 8/2011 |
| WO | 2011/143574 A2 | 11/2011 |

OTHER PUBLICATIONS

Marksteiner et al.; "Cerebrospinal Fluid Biomarkers for Diagnosis of Alzheimer's Disease: Beta-Amyloid(1-42), Tau, Phospho-Tau-181 and Total Protein"; Drugs of Today 2007, vol. 43, No. 6, pp. 423-431.
Welge et al.; "Combined SCF tau, p-tau181 and amyloid-beta 38/40/42 for diagnosing Alzheimer's disease"; Journal of Neural Transmission, 2009, vol. 116, No. 2, pp. 203-212.
Hampel et al.; "Core candidate neurochemical and imaging biomarkers of Alzheimer's disease"; Alzheimer's and Dementia 2008, vol. 4, No. 1, pp. 38-48.
Combarros et al.; "Replication by the Epistasis Project of the interaction between the genes for IL-6 and IL-10 in the risk of Alzheimer's disease"; Journal of Neuroinflammation, 2009, vol. 6, No. 22, entire article.
Malaguarnera et al.; "Interleukin-18 and transforming growth factor-beta 1 plasma levels in Alzheimer's disease and vascular dementia"; Neuropathology 2006, vol. 26, No. 4, pp. 307-312.
Mateo et al.; "Low serum VEGF levels are associated with Alzheimer's disease"; Acta Neurologica Scandinavica 2007, vol. 116, No. 1, pp. 56-58.
Luppi et al.; "Growth factors decrease in subjects with mild to moderate Alzheimer's disease (AD): Potential correction with dehydroepiandrosterone-sulphate (DHEAS)"; Archives of Gerontology and Geriatrics, 2009, vol. 49, supplement 1, pp. 173-184.
Mancinella et al.; "Is there a relationship between high c-reactive protein (CRP) levels and dementia?"; Archives of Gerontology and Geriatrics, 2009, vol. 49, supplement 1, pp. 185-194.
Ray et al.; "Classification and prediction of clinical Alzheimer's diagnosis based on plasma signaling proteins"; Nature Medicine, 2007, vol. 13, No. 11, pp. 1359-1362.
Araki et al.; "Determination of free and total homocysteine in human plasma by high-performance liquid chromatography with fluorescence detection"; Journal of Chromatography B: Biomedical Sciences and Applications, 1987, vol. 422, pp. 43-52, Abstract.
Anisman et al.; "Neurotransmitter, peptide and cytokine processes in relation to depressive disorder: Comorbidity between depression and neurodegenerative disorders"; Progress in Neurobiology, vol. 85, No. 1, May 1, 2008, pp. 1-74.
Kuang-Den Chen et al.; "Gene expression profiling of peripheral blood leukocytes identifies and validates ABCB1 as a novel biomarker for Alzheimer's disease"; Neurobiology of Disease, vol. 43, No. 3, May 28, 2011, pp. 698-705.
Morimoto et al.; "Expression profiles of cytokines in the brains of Alzheimer's disease (AD) patients compared to the brains of non-demented patients with and without increasing AD pathology"; Journal of Alzheimer's Disease, vol. 25, No. 1, 2011, pp. 59-76.
Sutinen et al.; "Pro-inflammatory interleukin-18 increases Alzheimer's disease-associated amyloid-[beta] production in human neuron-like cells"; Journal of Neuroinflammation, vol. 9, No. 1, Aug. 16, 2012, pp. 1-14.
Blasko et al.; "Measurement of thirteen biological markers in CSF of patients with Alzheimer's disease and other dementias"; Dementia and Geriatric Cognitive Disorders, vol. 21, No. 1, Jan. 1, 2006, pp. 9-15.

(Continued)

*Primary Examiner* — Olga N Chernyshev
(74) *Attorney, Agent, or Firm* — W & C IP

(57) ABSTRACT

A method for diagnosing of or for determining the risk of developing Alzheimer's disease, as well as for determining the presence of severe AD in a subject involves at least four specific biomarkers being measured. A kit or an array comprising a detecting means, in particular antibodies, for at least four specific biomarkers can be used for the diagnosis. Further, a computer program product and a computer implemented method for diagnosing of or determining the risk of developing Alzheimer's disease may be employed.

6 Claims, 1 Drawing Sheet

(56) References Cited

OTHER PUBLICATIONS

Galimberti et al; "Serum MCP-1 levels are increased in mild cognitive impairment and mild Alzheimer's disease"; Neurobiology of Aging, vol. 27, No. 12, Dec. 1, 2006, pp. 1763-1768.

Swardfager et al.; "A Meta-Analysis of Cytokines in Alzheimer's Disease"; Biological Psychiatry, vol. 68, No. 10, Nov. 15, 2010, pp. 930-941.

Galimberti et al: "Serum MCP-1 levels are increased in mild cognitive impairment and mild Alzheimer's disease", Elsevier, Neurobiology of Aging, vol. 72, pp. 1763-1768, 2006.

Huang et al: "Decreased serum levels of the angiogenic factors VEGF and TGF-β1 in Alzheimer's disease and amnestic mild cognitive impariment", Neuroscience Letters, vol. 550, pp. 60-63, 2013.

Swardfager et al: "A Meta-Analysis of Cytokines in Alzeimer's Disease", Biol Psychiatry, vol. 68, pp. 930-941, 2010.

Alvarez et al: "Serum TNF-alpha levels are increased and correlate negatively with free IGF-I in Alzheimer disease", Elsevier, Neurobiology of Aging, vol. 28, pp. 533-536, 2007.

Laske et al: "BDNG serum and CSF concentrations in Alzheimer's disease, normal pressure hydrocephalus and healthy controls", Elsevier, Journal of Psychiatric Research, vol. 41, pp. 387-394, 2007.

Blasko et al: "Measurement of Thirteen Bilogical Markers in CSF of Patients with Alzheimer's Disease and Other Dimentias", Dementia and Geriatric Cognitive Disorders, vol. 21, pp. 9-15, Feb. 2006.

Sutinen et al: "Pro-inflammatory interleukin-18 increses Alzheimer's disease-associated amyloid-β production in human neuron-like cells", Journal of Neuroinflammation, vol. 9, No. 199, pp. 1-14, 2012.

Galimberti et al: "Serum MCP-1 levels are increases in mild cognitive impairment and mild Alzheimer's disease", Neurobiology of Aging, vol. 27, pp. 1763-1768, 2006.

Swardfager et al: "A Meta-Analysis of Cytokines in Alzheimer's Disease", Biological Psychiatryvol. 68, pp. 930-941, 2010.

Huang et al: "Decreased serum levels of the angiogenic factors VEGF and TFG-β1 in Alzheimer's disease and amnestic mild cognitive impariment", Neuroscience Letters, vol. 55, pp. 60-63, 2013.

Laske et al: "BDNF serum and CSF concentrations in Alzheimer's disease, normal pressure hydrocephalus and healthy controls", Journal of Psychiatric Research, vol. 41, pp. 387-394, 2007.

BIOMARKER AND METHODS FOR EARLY DIAGNOSIS OF ALZHEIMER'S DISEASE

CROSS-REFERENCE TO RELATED APPLICATIONS

This application is a continuation-in-part (CIP) application of international application PCT/EP2015/051677 filed Jan. 28, 2015 which claims priority to European application 14152770.5 filed Jan. 28, 2014 and U.S. Patent Application 61/932,307 filed Jan. 28, 2014, the complete contents of which are herein incorporated by reference.

FIELD OF THE INVENTION

The present invention relates in a first aspect to a method for diagnosing of or for determining the risk of developing Alzheimer's disease or for determining the presence of severe Alzheimer's disease in a subject whereby a combination of at least four specific biomarkers are measured, thus, allowing to determine the treatment course of said subject. In addition, a kit as well as an array is provided comprising detecting means, in particular antibodies, for at least four specific biomarkers. Further, a computer program product and a computer implemented method for diagnosing of or determining the risk of developing Alzheimer's disease or for determining the presence of severe Alzheimer's disease is provided.

BACKGROUND

Alzheimer's disease (AD) is a progressive brain disease with a huge cost to human lives. The impact of the disease is also a growing concern for the governments of developing countries, in particular due to the increasingly high number of elderly citizens at risk. Alzheimer's disease is the most common form of dementia, a common term for memory loss and other cognitive impairments. Generally, dementia include the form of vascular dementia and degenerative dementia including Alzheimer's disease or Alzheimer's dementia. Different Types of dementia are described as amyloidopathy (Alzheimer's dementia), tauopathy (Lewy body disease, Creutzfeld-Jacob disease, Pick's disease), and synucleinopathy (Parkinson's disease).

The biggest risk factor for dementia is age. People over the age of 85 are more likely to experience the condition, although some forms of dementia occur in people under the age of 50. Some individuals are genetically more susceptible to develop certain forms of dementia, such as Alzheimer's and Huntington's diseases. Additionally, several factors can cause temporary or permanent dementia, such as brain injuries (including damage caused by stroke), malnutrition, infections, reaction to medication, poisoning, brain tumor or lesion.

Alzheimer's disease is a chronic progressive neurodegenerative disease and it is the most prevalent type of dementia. Current diagnostic means, including neuroimaging methods, are continuously improving. Nevertheless, it is still a challenge to increase the sensitivity and specificity of a diagnosis of Alzheimer's disease. Two diagnostic areas are especially challenging: first, differentiating early stages of Alzheimer's disease from mild cognitive impairment and normal aging; and second, increasing diagnostic specificity especially when similar clinical symptoms are shared by various types of dementia. To date, the analysis of beta-amyloid(1-42), total tau and phospho-tau-181 from cerebrospinal fluid (CSF) are the best biological markers to diagnose Alzheimer's disease and differentiate it from other forms of dementia with a high reliability and validity. Marksteiner J. et al. (Drugs Today 43(6):423-31, 2007) review the use of CSF biomarkers and of putative blood-related markers. It is suggested that the risk of mild cognitive impairment is influenced by tau protein gene variations and that mild cognitive impairment shares a common genetic background with Alzheimer's disease. This may help elucidating the genetic risk to cognitive decline and designing effective clinical trials. Welge V. et al. (J. Neural. Transm. 116(2): 203-12, 2009) reported that for cerebrospinal fluid (CSF) concentrations, the ratio Abeta1-42/Abeta1-38/p-tau powerfully discriminates Alzheimer's disease (AD) from non-Alzheimer dementia patients and fulfils the accuracy requirements for an applicable screening and differential diagnostic AD biomarker.

The Alzheimer's association provides seven stages during the course of disease, namely, 1: no impairment, 2 very mild decline (early stage), 3 mild decline, 4 moderate decline, 5 moderately severe decline, 6 severe decline, and 7 very severe decline.

Early detection of neurodegenerative disorders would enable more effective treatment of patients. Recent studies have demonstrated that disorders like Alzheimer's disease are characterized by a pre-symptomatic phase, likely lasting years, during which neuronal degeneration is occurring but before clinical symptoms appear. This presents both a challenge—how to identify individuals during this preclinical period—and an opportunity. Preventive therapy could be started during the preclinical period before disease symptoms appear. Therefore, a major goal of clinical research is to improve early detection of these diseases by developing tools to move diagnosis backward in the neurodegeneration temporal course. Furthermore, early identification of individuals being at risk of developing Alzheimer's disease is highly desired. It is described in the art that AD prophylaxes and treatment is more effective in patients with early detection of said neurodegenerative disorder as well as of delaying on said end progression of AD.

Aggregated amyloid-beta (Abeta) peptide is implicated in the pathology of Alzheimer's disease. In vitro and in vivo, these aggregates are found in a variety of morphologies, including globular oligomers and linear fibrils, which possess distinct biological activities. Diagnosis and monitoring of sporadic Alzheimer's disease (AD) have long depended on clinical examination of individuals with end-stage disease. However, upcoming anti-AD therapies are optimally initiated when individuals show very mild signs of neurodegeneration. There is a developing consensus for cerebrospinal fluid amyloid-beta (Abeta) as a core biomarker for the mild cognitive impairment stage of AD. Abeta is directly involved in the pathogenesis of AD or tightly correlated with other primary pathogenic factors. It is produced from amyloid precursor protein (APP) by proteolytic processing that depends on the beta-site APP-cleaving enzyme 1 and the gamma-secretase complex, and is degraded by a broad range of proteases.

The 40 and 42 amino-acid residue forms of amyloid-beta (Abeta(1-40) and Abeta(1-42)) in cerebrospinal fluid (CSF) have been proposed as potential biomarkers of Alzheimer's disease (AD). Quantitative analyses of Abeta peptides in CSF have relied almost exclusively on the use of immunosorbent-based assays such as the enzyme-linked immunosorbent assay (ELISA) procedure. However, due to the property of the Abeta peptides to readily self-aggregate or bind to other proteins and glassware, such analyses are extremely challenging. Analyses are further complicated by the potential of the peptides to undergo post-translational modifications and the possibility for cross-reaction in the ELISA assays with endogenous components of the CSF. Recent findings suggest that decreased plasma Abeta(1-42) relative to Abeta(1-40) might increase the risk of AD (Hampel H. et al., Alzheimers Dement. 4(1):38-48, 2008).

Tumor necrosis factor alpha (TNF-alpha) is a multifunctional pro-inflammatory cytokine that belongs to the tumor necrosis factor (TNF) superfamily. This cytokine is mainly secreted by macrophages. It is involved in the regulation of a wide spectrum of biological processes including cell proliferation, differentiation, apoptosis, lipid metabolism, and coagulation. This cytokine has been implicated in a variety of diseases, including autoimmune diseases, insulin resistance, and cancer. Knockout studies in mice also suggested the neuroprotective function of this cytokine.

The concept of inflammation as a major factor in Alzheimer's disease (AD) has heretofore been based on post mortem findings of autodestructive changes associated with the lesions coupled with epidemiological evidence of a protective effect of anti-inflammatory agents. Now there is evidence that the risk of AD is substantially influenced by a total of 10 polymorphisms in the inflammatory agents interleukin 1 alpha, interleukin 1 beta, interleukin 6, tumor necrosis factor alpha, alpha(2)-macroglobulin, and alpha(1)-antichymotrypsin. The polymorphisms are all common ones.

WO 2005/052292 and WO 2006/133423 describe methods and compositions for diagnosis, stratification, and monitoring of AD and other neurological disorders in body fluids. For example, EP 2 211 183 B1 stemming from the above WO application identifies methods for diagnosing and monitoring of AD wherein as a biomarker insulin-like growth factor binding protein 2 (EGFBP-2) is measured. The referenced patent application provides a large number of possible biomarker which should be allegedly suitable for diagnosing neurological disorders including AD. However, a specific set of biomarkers allowing diagnosis and prediction of AD with high accuracy is not disclosed. In addition, Thambisetty, N., et al, biomarkers and medicine, future medicine, London, Volume 4, No. 1, pages 65 to 79, disclose blood based biomarkers of AD: Challenging but feasible. WO 2009/149185 identifies dual variable domain immunoglobulins and uses thereof.

Recent findings have suggested an involvement of brain-derived neurotrophic factor (BDNF) in the pathogenesis of Alzheimer's disease (AD). BDNF is an endogenous protein involved in the maintenance of neuronal function, synaptic plasticity and structural integrity in the adult brain. BDNF serum and cerebrospinal fluid (CSF) concentrations were assessed by a sensitive ELISA in 27 AD patients in comparison to 9 normal pressure hydrocephalus (NPH) patients and 28 age-matched healthy controls. A significant decrease of BDNF serum concentration in AD (18.6 ng/ml) and NPH patients (18.1 ng/ml) was found as compared to healthy controls (21.3 ng/ml; p=0.041/p=0.017). BDNF serum concentrations did not correlate with CSF levels, age or mini mental state examination (MMSE) scores both in AD and NPH patients. The decrease of BDNF serum levels in AD and NPH may reflect a lack of trophic support and thus contribute to progressive degeneration in both diseases.

Chronic inflammation is a characteristic of Alzheimer's disease (AD). An interaction associated with the risk of AD has been reported between polymorphisms in the regulatory regions of the genes for the pro-inflammatory cytokine, interleukin-6 (IL-6), and the anti-inflammatory cytokine, interleukin-10 (IL-10). A dysregulation of both IL-6 and IL-10 in some elderly people, due in part to genetic variations in the two genes, may contribute to the development of AD (Cambarros O. et al., J. Neuroinflammation 23(6):22, 2009).

IL-6 (also named interferon beta 2) is highly elevated in Alzheimer's disease (AD) and has strong correlation to other diseases such as diabetes. IL-6 has also correlations to other neurodegenerative diseases and depression. A role in Alzheimer's disease (AD) is also suspected for the interleukins IL-10, IL-18 and vascular epidermal growth factor (VEGF). Malaguera L. et al. (Neuropathology 26(4):307-12, 2006) determined that the levels of IL-18 was significantly elevated in patients with AD and vascular dementia compared to non-demented, age-matched subjects.

Mateo et al. (Acta Neurol. Scand. 116(1):56-8, 2007) described that vascular endothelial growth factor (VEGF) determines important neurotrophic and neuroprotective actions. Low serum VEGF levels are associated with Alzheimer's disease.

The integrity of neuroprotection is an important component against the development of cognitive disorders and AD. An Alzheimer's disease patient group demonstrated at baseline a severe reduction of insulin-like growth factor-1 (IGF-1) (3.7±1.2 pg/ml), vascular endothelial growth factor (VEGF) (63±18 pg/ml) and TGF-beta 1 (33±10 pg/ml) compared to healthy elderly subjects (IGF-1, 9.5±2.4 pg/ml; VEGF, 105±31 pg/ml; and TGF-beta 1, 68±18 pg/ml). Significant positive correlations between IGF-1 and VEGF concentrations were found both in healthy subjects (r=0.87, p<0.001) and in AD subjects (Luppi C. et al., Arch. Gerontol. Geriatr. 49(Suppl. 1):173-84, 2009).

Elevations in plasma homocysteine are associated with common problems seen with aging, such as cognitive impairment, dementia, depression, osteoporotic fractures, and functional decline. It is known that homocysteine levels are higher in vascular dementia patients than in Alzheimer's disease (AD) patients or controls. Elevated plasma homocysteine concentrations and low serum folate concentrations are independent predictors of the development of dementia and AD. The normal range of plasma homocysteine level is 5-15 μmol/L, for AD patients above 15 μmol/L.

Monocyte chemotactic protein-1 (MCP-1) is highly induced in a variety of diseases that feature monocyte-rich cellular infiltrates such as atherosclerosis, congestive heart failure and rheumatoid arthritis.

The detection of elevated levels of C-reactive protein (CRP) in serum is not specific for any particular disease. It is a useful indicator of inflammatory processes. Plasma CRP is associated with prevalent mild cognitive impairment (MCI) and with non-amnestic MCI in elderly, non-demented persons in a population-based setting. These findings suggest the involvement of inflammation in the pathogenesis of MCI. High plasma CRP level is associated with accelerated cognitive decline and increased risk for dementia in patients with MCI. AD patients had higher CRP levels than vascular dementia patients (4.2±0.6 vs. 1.7±0.2, p<0.001, respectively). Stepwise multiple logistic regression analysis showed that dementia (odds ratio=OR=4.965, 95% confidence interval=CI=1.402-13.23, p=0.004), fibrinogen (OR=1.011, CI=1.007-1.015, p<0.001), and age (OR=1.158, CI=1.063-1.261, p<0.001) are independently correlated with high levels of CRP. The study suggests that inflammation may have a pathogenetic role in AD (Mancinella A. et al., Arch. Gerontol. Geriatr. 49(Suppl 1):185-94, 2009).

There is no current cure for Alzheimer's disease, but there are drug and non-drug based approaches for its treatment. In general the drug treatments are directed at slowing the progression of symptoms. Several biomarkers are well proved to be effective in a large group of patients but success is directly correlated with identifying the disease carriers at its early stages. This justifies the need for timely and accurate forms of diagnosis via molecular means, Ray S. et al., Nat. Med. 13(11):1359-62, 2007. At present, the drug approaches are based mainly on two principles: cholinesterase inhibitors, like donepezil, galantamine, and rivastamine as well as NMDA receptor antagonists like memantine. Further, non-drug based approaches include psychological therapies like psychotherapy, counseling and cognitive behavioral therapy. Other types of mental training are known but also exercises and diet.

To conclude, improved diagnostic screening for early Alzheimer's disease has a number of benefits. Early diagnosis allows people in the early stages of the disease to contribute to the decision making process about medication. Existing medications work best, if they are going to work at all, in the early stages of the disease. Early detection allows early intervention. As medications are developed it could well be that in the future early detection will prevent the irreversible damage to the brain that occurs as Alzheimer's disease progresses. Thus, there is an ongoing need for methods and test systems allowing diagnosing AD at an early stage with high specificity, thus, allowing determination of the treatment regimen in case of diagnosing positively AD. Furthermore, to allow differentiation of AD from other types of dementia, new methods and assays are required. That is, identifying later steps of AD is of help for allowing determination of the treatment regimen.

BRIEF DESCRIPTION OF THE PRESENT INVENTION

The present invention relates in a first aspect to a method for diagnosing of or predicting the risk of development of Alzheimer's disease (AD) and determining the treatment regimen of AD comprising
  a) measuring the level or amount of AD biomarker in a biological sample from a subject; and
  b) determining or diagnosing the presence or the risk of developing of AD based on the level or amount of said biomarker,
  c) determining the treatment regimen for AD in case of indication of AD, whereby the biomarker are at least four biomarker selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), and, in a first embodiment, whereby an increase of IL-18 and/or MCP-1, and/or the decrease of BDNF, IGF-1, VEGF and/or TGF-beta 1 is indicative for the presence or risk of development of AD. In addition, homocysteine may be used as a further biomarker for verification of the diagnosis. In AD patients, homocysteine level or amounts are decreased.

Furthermore, the present invention relates to a method for determining the status of Alzheimer's disease (AD) in a subject for determining the treatment regimen, comprising
  a) measuring the level or amount of AD biomarker in a biological sample from a subject; and
  b) determining the presence or the status of AD with high specificity based on the level or amount of said biomarker,
    whereby the AD biomarker are at least four biomarker selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), and whereby an increase of IL-18, and/or VEGF, and/or the decrease of BDNF, IGF-1, MCP-1 and/or TGF-beta 1 is indicative for the presence of severe AD,
  c) determining the type of treatment, the treatment regimen, in the subject based on the indication of the presence or the states of AD according to step b.

That is, in another embodiment, verification of suffering from late phases of AD starting from severe AD in dementia patients is characterised in an increase in IL-18 and/or VEGF and/or decrease of BNDF, IGF-1, MCP-1 and/or TGF-beta 1.

The combination of at least 4 of the referenced marker allows on the one hand the early diagnosis and detection of the risk of developing AD with high specificity of at least 90%, and, on the other hand, determining the presence of severe with high specificity of at least 90%.

It is preferred that at least four, like at least five or all biomarker out of the biomarker BDNF, IGF-1, TGF-beta 1, VEGF, IL-18 and MCP-1 are measured.

The biomarker molecular signature comprising at least four of the biomarkers identified above achieves on average, 90%, like 95%, in particular 96% accuracy, like sensitivity, in predicting clinical AD. At least, the biomarker molecular signature allows early detection of the risk for Alzheimer's disease in an early onset of a suitable therapy as well as for determining the presence of severe AD.

In addition, in a second aspect, the present invention relates to a kit for use in diagnosing or predicting the risk of developing Alzheimer's disease as well as for determining the presence of severe AD and in determining the treatment regimen of a subject comprising detection means for at least four of the biomarkers selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), and, optionally, homocysteine, for use in diagnosing or determining the risk of development of AD, optionally, containing instructions how to use the kit in a method according to the present invention for diagnosing the presence or the risk of development of AD as well as for determining the presence of severe AD.

Moreover, the present invention relates to the use in vitro of at least four, like at least five, of the biomarker as defined herein for use in the diagnosis, with assessment or therapy control of AD by determining the level or amount of said biomarker in a biological sample of an individual and determining an increase or decrease of at least four, like at least five of said biomarker compared to reference a level or amounts of said biomarker. The biomarker is indicative for AD when the level or amount is above or below, respectively, of a cut-off for said specific biomarker. Moreover, the present invention relates to an array comprising means for detecting at least four of the biomarkers according to the present invention, in particular an array or kit wherein the detection means are antibodies and detection of said biomarkers is conducted immunologically.

Moreover, the present invention relates to a computer implemented method of diagnosing of or determining the risk of developing AD comprising the steps of:

a) obtaining data of measured level or amount of at least four of the AD biomarker according to the present invention in a biological sample of a subject and, optionally, of controls;

b) computing the data of step a) by comparing the level or amount of the biomarker in said sample with a cut off value obtained from a data base or obtained as a measured level or a measured amount of a cut-off control.

c) identifying biomarker which level or amount is increased or decreased above or below the cut off level.

Finally, the present invention relates to a computer medium or computer program product having computer executable instructions for performing the method according to the present invention.

DETAILED DESCRIPTION

Figure 1:
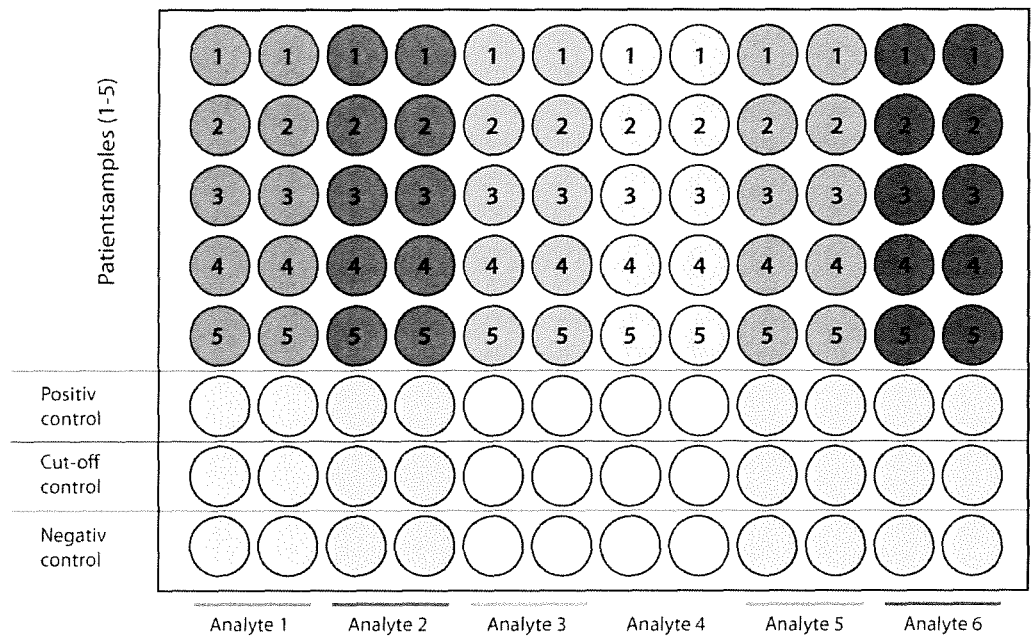
In FIG. 1 a scheme of a microtiter plate is provided showing the allocation of each probe. Each sample is measured in duplicate. Further, a positive control, a negative control and a cut off control is present allowing having internal controls on the plate. In the present case, 5 patient samples are tested.

As used herein, the term "Alzheimer's disease" means a degenerative brain disease that kills nerve cells in the cerebral cortex to atrophy or reduces gyri (ridges on the cerebral cortex) in the frontal and temporal lobes of the cerebrum, in particular as defined by the NINCDS-ARDA criteria (National Institute of Neurological and Communicative Disorders and Stroke, and Alzheimer's Disease and Related Disorders Association).

As used herein, the term "diagnosis" means identifying the presence or features of pathological states. With respect to the objects of the present invention "diagnosis" means determination of the risk to get Alzheimer's disease based on ex vivo analysis of body fluids.

As used herein the term "biomarker" means a substance capable of indicating a disease state. In the context of the present invention directed to diagnosing Alzheimer's disease, "biomarker" means a substance indicating whether brain cells are in a normal state or attacked by Alzheimer's disease. "Biomarker" includes polypeptides and glycoproteins, the quantities of which increase or decrease in patients suffering from Alzheimer's disease or prone to be afflicted by Alzheimer's disease as compared to normal healthy subjects.

As used herein, the term "blood" includes whole blood, serum and plasma.

As used herein, the term "antibody" means an immunoglobulin specifically binding to an antigenic region of a biomolecule. With respect to the object of the present invention, the antibody is specifically binding to a biomarker, and includes a polyclonal antibody, a monoclonal antibody, and a recombinant antibody. In addition, the antibody of the present invention includes functional fragments of antibody molecules, as well as complete forms having two full-length light chains and two full-length heavy chains. The functional fragment of antibody molecules means a fragment retaining at least the antigen-binding function, and includes Fab, $F(ab')_2$, Fv, and the like fragments.

As used herein, the term "antigen-antibody complex" means a binding product of a biomarker to an antibody recognizing it.

As used herein, the terms "comprise" or "comprising" and the terms "contain" or "containing" include the embodiments of "consist" and "consisting of".

The term "cut-off level" as used herein refers to the relative or absolute level determined to allow distinguishing between individuals suffering from AD or being at risk of developing AD. The cut-off level is given as a fold difference in case of relative levels or as a specific value in case of absolute values, e.g. in case of protein level expressed as ng or pg/ml. Values being below or above the cut-off level, respectively, as indicated herein, are regarded as allowing diagnosis of AD or determining the risk of developing AD, or allowing for determining the presence of severe AD, and, eventually, therapy control in AD patients.

As used herein, the term "AD biomarker" refers to a biomarker that is an AD diagnosis biomarker.

As used herein, the term "predicting" refers to making a finding that an individual has a significantly enhanced probability of developing a biological disease.

As used herein, the term "biological sample" encompasses a variety of a sample types obtained from an individual and can be used in a diagnostic or monitoring assay. Biological fluid sample encompasses blood, cerebrospinal fluid (CSF), urine and other liquid samples of biological origin. If required, the samples may be treated in advance for example for enrichment or separation.

An "individual" or "subject" is a mammal, more preferably a human, the term individual or subject are used herein interchangeably.

As used herein, a "reference value" can be an absolute value, a relative value, a value that has an upper or lower limit, a range of values, an average value, a median value, a mean value, or a value as compared to a particular control or baseline value. A reference value can be based on an individual sample value, such as for example a value obtained from a sample from the individual to be tested obtained at an earlier time point or a value obtained from a sample from an AD patient other than the individual being tested or a normal individual, that is an individual not diagnosed with AD. The reference value can be based on a large number of samples, such as from AD patients or normal individuals or based on a pool of samples including the sample to be tested.

As used herein, "a", "an", and "the" can mean singular or plural unless indicated otherwise.

As used herein, the phrase, fold difference, refers to numerical representation of the magnitude difference between a measured value and a reference value for an AD biomarker. Fold difference is calculated mathematically by division of the numeric measured value with the numeric reference value. For example, if a measured value for an AD biomarker is 20 nanograms/milliliter (ng/ml) and the reference value is 10 ng/ml, the fold difference is two. Alternatively, if a measured value for an AD biomarker is 10 ng/ml and the reference value is 20 ng/ml, the fold difference is 50%.

As used herein, the phrase "determining the treatment course" or "determining the treatment regimen" refers to the step of stipulating the therapy of a subject which has been determined to be at risk of developing AD or having Ad. This step includes specifying the type of therapy, like drug based or non-drug based therapy as well as the therapy regimen. The step of determining the treatment course may include the step of treating the subject accordingly.

That is, the method according to the present invention may further include the step of treating the subject being at risk of developing AD or diagnosed for AD with a suitable therapy as outlined herein.

The present inventors recognized that when measuring the level or amount of a combination of at least four biomarkers selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), and, optionally, homocysteine, and, in a first embodiment, whereby an increase of IL-18, MCP-1, and/or homocysteine and/or the decrease of BDNF, IGF-1, VEGF and/or TGF-beta 1 in a biological sample from a subject is determined, it is possible to diagnose early AD or determine the risk of developing Alzheimer's disease with higher specificity than using a combination of 1, 2 or 3 marker only. In particular, it has been identified that Alzheimer's disease or the risk of developing Alzheimer's disease is linked with changes in the expression level of the six marker specified herein, namely, an increase of IL-18, MCP-1, and/or homocysteine as well as a decrease of BDNF, IGF-1, VEGF and/or TGF-beta 1. Further, it has been recognized that when combining at least four, preferably at least five, like all six biomarker of brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), the specificity and sensitivity is sufficiently high to enable diagnosis or prognosis of AD while each of the biomarker alone may be altered in different diseases and conditions other than AD. Furthermore, the amount or level of homocysteine may be used to confirm the results.

In a further aspect, the method according to the present invention allows to differentiate AD from other forms of established dementia and to determine late stages, namely severe stage and very severe stage of AD. That is, established AD is characterized in a decrease of BDNF, IGF-1, MCP-1 and/or TGF-beta 1 and/or increase of VEGF and/or IL-18. Table 2 shows the measured amount of said protein in serum samples of normal healthy control group and severe Alzheimer disease patient group. In this connection, it is noted that the terms "severe" and "established" are used interchangeably herein.

TABLE 2

| Biomarkerprotein | Normal healthy control group | Alzheimers disease group | Increase or decrease in AD |
|---|---|---|---|
| BDNF | 22.8 +/− 1.6 ng/ml | 2-12 ng/ml | decrease |
| IGF-1 | 70-200 ng/ml | 30-60 ng/ml | decrease |
| VEGF | 314 +/− 15 pg/ml | 400-2000 pg/ml | increase, vasculäre AD |
| TGF-beta 1 | 70-200 pg/ml | 3-30 pg/ml | decrease |
| MCP-1 | 160 pg/ml | 60 pg/ml | decrease |
| IL-18 | 100-200 pg/ml | 320 pg/ml | increase |

In particular, when at least four biomarker of the six biomarker as defined herein are increased or decreased, respectively, the accuracy of diagnosing of AD or determining the risk of developing AD as well as for determining the presence of severe AD is very high and it is possible to monitor therapy. In particular, the accuracy is at least 90%, for example at least 95% and in some instances at least 96%. For example, the sensitivity of the method is in the range of at least 90%, like at least 95%, e.g. at least 96%. In addition, the specificity of the method according to the present invention is at least 85%, like at least 90%, e.g. at least 92% or at least 95%. Hence, the specific combination of the biomarker according to the present invention allows to diagnose or determine AD with high accuracy, in particular, with high accuracy compared to the prior art.

If desired, the biomarker according to the present invention may be combined with other biomarker known in the art and described as being suitable AD biomarker. The person skilled in the art is well aware of suitable biomarker which may be combined with the biomarker as defined herein.

A bunch of biomarker have been described in the art as being altered in its level or amount in subjects suffering from AD compared to control groups. However, specificity and sensitivity, i.e. accuracy, thereof is not sufficient or satisfactory for diagnosing of or for determining the risk of developing AD in a subject in particular in view of the fact that the single biomarker may be altered in its expression levels or amounts in other diseases as well.

In contrast, the set of biomarker according to the present invention, namely, the biomarker being at least four of the biomarkers according to the present invention allows to diagnose AD early as well as for determining the presence of severe AD with high accuracy and specificity.

Further, it is noted that the term measuring, determining or diagnosing includes the step of physically measuring, physically determining or physically diagnosing the level or amount of the AD biomarker. That is, the method includes the step of measuring a level or amount of the AD biomarker with known methods useful for measuring a level or amount and using said measured level or amounts to determine or to diagnose accordingly.

In a preferred embodiment, the biomarkers are determined in form of its peptide or protein. However, it is also possible to measure the level or amount of the AD biomarker on the nucleic acid level, e.g. based on mRNA level or amount in the biological sample.

According to the present invention, the method disclosed herein relates to in vitro and/or in vivo methods, respectively. Preferably, the methods are in vitro methods based on samples obtained from the individuals and provided in vitro.

The present inventors aimed in demonstrating that measuring and determining the level or amount of specific AD biomarker, namely of brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1) allows for diagnosing or predicting the risk of developing AD as well as allowing differentiation of AD from other type of dementia and determining late stages of AD.

In a preferred embodiment, the combination of biomarkers as identified below is measured:
  a) BDNF, IGF-1, VEGF and TGF-beta 1;
  b) BDNF, IGF-1, VEGF, IL-18 and MCP-1;
  c) BDNF, VEGF, TGF-beta 1, IL-18 and MCP-1;
  d) IGF-1, VEGF, TGF-beta 1, IL-18, MCP-1.

Another preferred embodiment includes the following combinations:
  e) BDNF, IGF-1, VEGF and MCP-1
  f) BDNF, IGF-1, TGF-beta 1, MCP-1
  g) BDNF, IGF-1, VEGF, TGF-beta 1, MCP-1.

In an embodiment of the present invention, the method includes measuring the level or amount of all biomarkers as defined herein. In addition, the level or amount of homocysteine is determined as well.

As mentioned, the biomarker signature, namely, the level or amount of the biomarker according to the present invention allows on average 96% accuracy in predicting clinical Alzheimer's disease, thus, allowing to determine the treatment regimen with higher accuracy. This can be used to confirm that a patient with obvious signs of a dementia is reflected by AD and it can furthermore be used to diagnose a patient with unclear syndromes or mild cognitive impairment, that such a patient has a substantial or even higher risk of contracting AD. Compared with the state of the art of diagnosing AD, the presently claimed biomarker has substantial advantages. For example, all the biomarkers are present in blood. They can be easily and reliably measured in blood or serum samples with standard equipment and, there is no need for analyzing tissue or cerebrospinal fluid.

In an embodiment of the present invention, the biological sample is selected from blood, tissue or body fluid. In a preferred embodiment, the biological sample is blood, in particular, blood serum.

As mentioned, in an embodiment, the biomarker IL-18, and MCP-1 as well as of homocysteine are increased in the sample of AD patients, in particular at early disease stage, like in the blood of the AD patient group, compared to the level or amount of said biomarker in a group of non-diseased humans used as control subjects. With established (severe) AD, the biomarker IL-18 and VEGF are increased.

Further, BDNF, IGF-1, TGF-beta1 and VEGF are present in lower quantity in the sample of AD patient groups, in particular at early disease stage compared to the quantity in the sample of a group of non-diseased humans. With established (severe) AD, the biomarker BDNF, IGF-1, TGF-beta 1 and MCP-1 are increased.

That is, while for the single biomarker a change of the amount or level compared to the control group or a reference group is in the range of up to 70% in the AD group, the combination of the biomarker as defined herein, namely, determining the change or alteration of the level or amount of at least four biomarker allow to increase accuracy of the diagnosis or determination of risk of developing AD for 90% or higher.

For example BDNF is reduced in almost 70% in the blood of AD patients in relation to control subjects. The cytokine shows a high significant relationship with age.

Table 1 shows the biomarker protein and the measured amount of said protein in serum samples of normal healthy control group and early Alzheimer disease patient group.

TABLE 1

| Biomarker protein | Normal healthy control group | Alzheimer's disease patient group | Increase or decrease in AD |
| --- | --- | --- | --- |
| BNDF | 21.3 ng/ml | 2-10 ng/ml | decreased |
| IGF-1 | 70-200 ng/ml | 60 ng/ml | decreased |
| VEGF | 309 pg/ml | 210 pg/ml | decreased |
| TGF-beta1 | 370 pg/ml | 10-80 pg/ml | decreased |
| MCP-1 | 160 pg/ml | 400-700 pg/ml | increased |
| Il-18 | 100-200 pg/ml | 320 pg/ml | increased |

The measurement of the level or amount according of the biomarker according to the present invention is conducted by known methods. For example in case of determining the level or amount on protein level, an immunoassay is conducted, for example, ELISA, RIA, radioimmunodiffusion, Western blotting, Ouchterlony immunodiffusion, rocket immunoelectrophoresis, immunohistostaining, immunoprecipitation assay, complement fixation assay, FACS, and protein chip assay as well as immunofluorescence assay, multiplex immunoassay, line assay or dot lot assay.

In a preferred embodiment, an ELISA is conducted. Typical examples of measuring means for measuring the level or amount of the biomarker include protein specific antibodies. Specific molecular antibodies are known in the art or may be prepared easily based on methods described in the art. Measuring protein level means measuring the quantity of proteins by using measuring means specifically binding to the proteins, such as an antibody. Said measuring method may be defined of anyone of the methods described above. Typically, said method includes the formation of antigen antibody complex and determining the complex by known methods.

The quantity of an antigen-antibody complex formation may be determined by measuring the signal size of a detection label or the expression label of a biomarker protein. That is, the antibody may be labelled with a detection label known in the art including but not limiting to the group of an enzyme, a fluorescence marker, a ligand, a luminant, a microparticle, and a redox molecule. Examples of the enzyme available as the detection label include, but are not limited to, D-glucosidase, urease, peroxidase, alkaline phosphatase, acetylcholinesterase, glucose oxidase, hexokinase, GDPase, RNase, luciferase, phosphofructokinase, phosphoenolpyruvate carboxylase, aspartate aminotransferase, and phosphoenolpyruvate decarboxylase. Examples of the fluorescence markers include, but are not limited to, fluorescein isothiocyanate, rhodamine, phycoerythrin, phycocyanin, allophycocyanin, and fluorescamin. Examples of a ligand include, but are not limited to, biotin, avidin, and biotin and avidin derivatives.

As described above, in order to measure levels of the kinds of proteins selected from the group consisting of the mentioned protein biomarkers, the present invention provides a composition comprising an agent specific to the biomarker proteins, such as an antibody, preferably in the form of a monoclonal antibody, recombinant antibody, or antibody fragment.

In an embodiment, the method according to the present invention comprises the step of comparing the level or amount of the AD biomarker measured in said biological sample with a reference level or amount of the biomarker. The reference label is
a) an average label obtained from a population that is not afflicted with AD; and/or
b) a mean or medium level from a group of individuals including AD patients.

In particular, it is determined whether the level or amount of the biomarker is above or below, respectively, of a cut-off level.

For example, tables 3 and 4 provide cut-off level when measuring the level or amount of the biomarker protein in a blood sample, like a blood serum sample in case of early diagnosis (table 3).

TABLE 3

| Biomarker protein | Increase or decrease in AD | Cut off to AD pathogenicity |
| --- | --- | --- |
| BNDF | decreased | <10 ng/ml |
| IGF-1 | decreased | <60 ng/ml |
| VEGF | decreased | <250 pg/ml |
| TGF-beta1 | decreased | <300 pg/ml |

TABLE 3-continued

| Biomarker protein | Increase or decrease in AD | Cut off to AD pathogenicity |
|---|---|---|
| MCP-1 | increased | >300 pg/ml |
| Il-18 | increased | >200 pg/ml |

For example, for BNDF, the amount is decreased at least 50%, e.g. from 20 ng/ml in a normal healthy control group to about 10 ng/ml or below in the AD patient group. For IGF-1, the change is about a decrease of more than 40%, e.g. from above 70 ng/ml to 60 ng/ml or below. VEGF, the decrease is about 18% or more, for example from 309 pg/ml to 250 pg/ml or below. For TGF-beta 1 the decrease is at least 20%, for example from 370 pg/ml to 300 pg/ml or below. For MCP-1 the increase is 40% or more, e.g. from 160 pg/ml to 300 pg/ml or more. For IL-18 the increase is at least 15%, for example to 200 pg/ml or more. Further, the level or amount of homocysteine may be determined for verifying or confirming the results obtained using the biomarker as defined herein.

In addition, table 4 shows the cut off level in case of patients with severe AD.

TABLE 4

| Biomarker | Increase or decrease in AD | Cut off to AD pathogenicity |
|---|---|---|
| BDNF | Decreased | <20 ng/ml |
| IGF-1 | Decreased | <90 ng/ml |
| VEGF | increased | >400 pg/ml |
| TGF-beta 1 | Decreased | <50 pg/ml |
| MCP-1 | Decreased | <100 pg/ml |
| IL-18 | Increased | >300 pg/ml |

Further, the step of determining the treatment course or the treatment regimen include the identification of a drug based or non-drug based therapy for the subject being at risk of developing or being diagnosed for AD. In addition, based on the stage of AD determined, the therapy course or therapy regimen may be adapted accordingly.

At present, various types of drug and non-drug based therapies are known. The drug based therapies are based mainly on two principles. The first principle is the administration of a cholinesterase inhibitor. FDA approved cholinesterase inhibitors include donepezil, galantamine and rivastamine. The principle is based on increasing the level of acetylcholine in the brain which is lowered in AD subjects.

Another medicament, memantine, is a representative of a NMDA receptor antagonist.

In addition, it is submitted that activation of CD4 T-cells allows to treat Alzheimer's disease since studies demonstrated that cytokines produced by these types of cells allow to regulate microglia activity. Hence, a new type of therapy is an activation of adaptive immune system with T-cells stimulation for example gamma interferon reduction. Hence, CD4 T-cell activation represents a suitable tool for treating AD. Other favorable therapy concepts include blocking prominent inflammatory cascade underlying the autoinflammation (TGF-beta 1) as well as improving the immunity through direct immune intervention, thus, balancing key cytokines like TGF-beta 1 and IL-18 with gamma interferon. Further, another approach is the reduction of the concentration of cholesterol in the brain, for example, cholesterol as part of LDLs. The reduction may be achieved by VEGF balancing or stimulation of the cholesterol hydroxylase accordingly.

Further, non-drug based therapies include exercises, stress management and appropriate nutrition or diets. That is, mental training, a specific diet and exercises as well as psychical training including counseling and psychotherapy have positive effects on the various steps of AD and, in particular, when being at risk of developing AD, namely, the early stages of AD.

Thus, the therapy includes non-drug based therapies as mentioned above. That is, the methods according to the present invention relating to the diagnosis of AD or determining the risk of development of AD as well as determining the status of AD includes further the step of determining the treatment regimen and, consequently, treating the subjects accordingly.

Further, sphingolipids are suggested as a form of therapy.

That is, the present invention relates to methods including the diagnosis of AD and, based on said diagnosis, treating the individuals supposed to be afflicted with AD or being at risk of developing AD with a therapy against AD including drug and non-drug based therapies.

In a further aspect, the present invention relates to a kit comprising detection means for at least four of the biomarker selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1) for use in diagnosing or determining the risk of development of AD, as well as for determining the presence of severe AD, optionally, containing instructions how to use the kit in a method according to the present invention for diagnosing the presence or the risk of development of AD, as well as for determining the presence of severe AD and, subsequently, determining the treatment course.

The inventive kit for detecting diagnostic biomarkers comprises antibodies specific to the above proteins and may further comprise a secondary antibody conjugated to a label, e.g. an enzyme, useful for a chromogenic reaction with a substrate; a chromogenic substrate solution to induce the chromogenic reaction with the label; a washing solution; and an enzyme reaction stop solution. It may further contain suitable microplates, standard solutions and protocols. In place of a secondary antibody conjugated to a label, the (primary) antibodies specific to the biomarkers described above and below may themselves be conjugated to a label.

The inventive kit for detecting diagnostic biomarkers can diagnose Alzheimer's disease by quantitatively or qualitatively analyzing an antigen through an antigen-antibody binding reaction, and the antigen-antibody binding reaction may be measured by a conventional method, such as ELISA (enzyme-linked immunosorbent assay) or sandwich assay. For example, the kit for detecting diagnostic biomarkers as described above or below may be provided in such a manner as to conduct ELISA for reacting with a recombinant monoclonal antibody protein by using a 96-well microtiter plate surface coated with an analyte and a control. As a receptor for the antigen-antibody binding reaction, a well plate of a polyvinyl or polystyrene resin, a nitrocellulose membrane, or a slide glass may be used.

A conventional label conducting a chromogenic reaction, such as HRP (horseradish peroxidase), alkaline phosphatase, colloidal gold, a fluorescent label such as fluorescein, FITC (poly L-lysine-flourescein isothiocyanate) or RITC (rhodamine-B isocyanate), or a dye may be preferably used as the label of the secondary antibody conjugate or as the label of the primary antibody conjugate.

The substrate producing the chromogenic reaction is chosen depending on the label. Particularly preferred substrates are those to be used with a peroxidase, e.g. with horseradish peroxidase, and are, for example, TMB (3,3',5,5'-tetramethylbenzidine), ABTS (2,2'-azino-bis(3-ethylbenzothiozoline-6-sulfonic acid)), or OPD (o-phenylenediamine). Preferably, the chromogenic substrate is prepared in a dissolved state in a buffer solution (for example 0.1 M sodium acetate, pH 5.5). HRP (horseradish peroxidase) used as the label of the antibody conjugate decomposes the chromogenic substrate, such as TMB, to produce a chromogenic precipitate in the presence of hydrogen peroxide. By checking the degree of precipitation of the chromogenic precipitate with naked eye, the presence or absence of the protein biomarker is detected. The color of TMB is measured at 450 nm, the color of ABTS at 420 nm, and the color of OPD at 492 nm. A sulfuric acid solution ($H_2SO_4$) may be preferably used as the peroxidase enzyme stop solution.

Alternatively alkaline phosphatase as the enzyme label and PNPP (paranitrophenylphosphate) as the chromogenic substrate may be used. The yellow color of nitrophenol can be measured at 405 nm. This reaction is stopped by adding sodium hydroxide.

The washing solution preferably comprises a phosphate buffer solution, NaCl, and Tween 20, and more preferably, is a buffer solution comprising 0.02 M phosphate buffer solution, 0.13 M NaCl, and 0.05% Tween 20. After the antigen-antibody binding reaction is performed to form an antigen-antibody complex, the antigen-antibody complex is reacted with the secondary antibody conjugate, and then is washed 3 to 6 times by adding an appropriate amount of washing solution to the reactor.

Other methods of determining the amount of biomarkers are also considered, in particular RIA (radioimmunoassay), Western blotting on polyacrylamide gel, immunoblotting, and immunohistochemical staining. The kits are adapted to the particular method considered for the quantitative determination of the biomarkers, as is well known in the art.

In a preferred embodiment of the present invention, the amount of a biomarker protein is measured by ELISA with horseradish peroxidase and a chromogenic substrate selected from TMB, ABTS and OPD.

As identified above, the detection means are for example antibodies in case of determining the level or amount of the biomarker on protein level. Alternatively, the detection means may be nucleic acid molecules in case of detecting a level or amount on nucleic acid level.

For example, the kit is an ELISA or other suitable immunoassay known to the person skilled in the art.

Moreover, the present invention provides an array, comprising means for detecting at least four of the biomarker as defined herein, for example detecting at least five of said biomarker, in particular, at least six of the biomarker as defined herein.

The kit or array according to present invention is particularly useful for conducting the method according to the present invention. In an embodiment of the kit or array, the detecting means are antibodies, like monoclonal antibodies specifically binding to the biomarkers as defined herein.

For example, an array according to the present invention may be a microtiter-plate.

Said microtiter-plate may allow determining the level or amount of the biomarker together with determining the level or amount of the positive control, a negative control and/or a cut-off control. Hence, said array allow determining an increase or decrease of said biomarker, in particular, an increase or decrease of said biomarker below or above a cut-off level, thus, allowing determining or diagnosing easily in the presence of or the risk of developing AD as well as for determining the presence of severe AD based on the level or amount of said biomarker. In FIG. 1 a scheme is provided showing a suitable microtiter-plate. As identified, patient samples 1 to 5 are tested with six analytes, namely analytes 1 to 6 being selected from the seven biomarkers according to the present invention. In addition, positive control as well as a negative control is provided. Moreover, to determine whether the level or amount of the biomarker in the sample is suitable for allowing determination or diagnosis of AD, a cut-off control is provided. Hence, this control on the same array allows determining easily whether the measured level or amount of the AD biomarker is suitable for diagnosis or not. This is particularly valuable for a computer implemented method or system.

That is, the present invention relates in another aspect to the use in vitro of at least four, like five, for example six or all of the biomarkers as defined herein for use in the diagnosis, risk assessment or therapy control of Alzheimer's disease and, eventually determining the treatment course of said subject by determining a level or amount of said biomarker in a biological sample of individual and determining an increase or decrease of said at least four, like at least five, like six or all of said biomarker compared to a reference level or amount of said biomarker whereby the reference level is an average level obtained from a population is not affected with AD; and/or medium level from a group of individuals including AD patients whereby a cut-off level of said individual biomarker is used to allow identification of an increase or decrease, accordingly. In an embodiment of the present invention, the cut-off level is reflected by a suitable cut-off control present as a control in the method according to the present invention, for example, as described in an array according to the present invention.

Moreover, the present invention relates to a computer implemented method of diagnosing of or determining the risk of developing AD comprising the steps of a) obtaining data of measured level or amount of at least four of the AD biomarker as defined herein, namely, brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), in a biological sample of a subject and, optionally, of controls;

b) computing the data of step a) by comparing the level or amount of the biomarker in said sample with a cut off value obtained from a data base or obtained as a measured level or measured amount of a cut-off control;

c) analysing and identifying biomarker which level or amount is increased or decreased above or below the cut off level.

Optionally the method comprises further the step of presenting the result for each of the biomarker or, simply, of a positive or negative diagnosis or risk assessment on an output unit, e.g. in form of coloured and highlighted presentation.

For example, the analysis is conducted by principal component analysis. The analysis may be accompanied by error analysis. Finally, the present invention relates to a computer medium or computer program product having computer executable instructions for performing the steps of the method according to the present invention.

In some embodiments, the comparison of the measured value and the reference value includes calculating a fold difference between the measured value and the referenced value to allow identification whether the measured value is above or below the cut-off level accordingly.

EXAMPLES

Example 1: Quantitative Protein Analysis of Blood Collected from Patients with Degenerative Brain Disease and from Normal Healthy Subjects Blood samples from patients with Alzheimer's disease and from a control group of healthy human subjects are collected with the consent of the patients and following applicable ethical guidelines.

A serum separator tube is used and the sample allowed to clot for 2 h at room temperature or overnight at 4° C. before centrifugation for 20 minutes at approximately 1000×g. The freshly prepared serum is immediately assayed or samples stored in aliquots at −20 or −80° C. Repeated freeze/thaw cycles should be avoided.

ELISA (sandwich ELISA to detect sample antigen) are performed using an antibody specific to the antigen of the collected samples of the following marker protein, BDNF, IGF-1, TGF-beta 1, VEGF, MCP-1 and IL-18.

Example 2: ELISA for BDNF, IGF-1, TGF-Beta 1, VEGF, IL-18 and MCP-1

A 1.0 ml (1 µg/ml) standard diluent in PBS, pH 7.4 of each antigen is prepared. It is kept for 10 min at room temperature, and shaken gently.

Pre-coated wells with antibodies for IL-18, TGF-beta 1, VEGF, BDNF, MCP-1, and IGF-1, respectively, are purchased from B&D Biosciences, Bachem, Novagen, Invitrogen, or GenScript or others.

100 µl of each 1:1, 1:2, 1:4, 1:8, 1:16, 1:32, and 1:64 dilutions of the mentioned 1 µg/ml standard antigen solutions are prepared and added to one well each (7 wells). The 8$^{th}$ well is reserved for a blank. The wells are sealed with the plate sealer and incubated for 2 h at room temperature with continuous shaking (700 rpm). After the incubation, the plate is aspirated, washed three times with 400 µl wash solution, and again aspirated. Then 100 µl of the respective anti-HRP-conjugated antibody is added to each well of the plate and incubated for 2 h at room temperature with shaking at 700 rpm. The contents of each well are aspirated. The plate is again washed three times prior to the addition of 200 µl of the OPD (o-phenylenediamine dihydrochloride) substrate solution. The OPD substrate solution is prepared by adding two 10 mg OPD tablets to the supplied OPD diluent, followed by the addition of 50 µl of 3% $H_2O_2$. The plate is then incubated for 20-25 minutes in the dark while the color develops. The color development is stopped with the addition of 100 µl of the stop solution (3 N sulfuric acid). The plate is read in a microplate reader at 492 nm.

In place of OPD, ABTS (2,2'-azino-bis(3-ethylbenzothiazoline-6-sulfonic acid)), TMB (3,3',5,5'-tetramethylbenzidine), or DAB (3,3'-diaminobenzidine) may be used as chromogenic substrates.

Alternatively alkaline phosphatase as the enzyme and PNPP (paranitrophenylphosphate) may be used. The yellow color of nitrophenol can be measured at 405 nm after 15 min at room temperature. This reaction is stopped by adding an equal volume of 0.75 M NaOH.

A standard curve is created from the standards on the plate and this is used to calculate the concentration of the title antigens in the samples.

Example 3: Testing Samples from Alzheimer's Disease Patients and Normal Healthy Subjects 96-well high binding Stripwell immunoassay plates (Corning Life Sciences, NY, or BD Bioscience) are pre-coated with the antibodies of each IL-18, TGF-beta 1, VEGF, BDNF, MCP-1, and IGF-1 at a concentration of 10 µg/ml (20 µl diluted 1:100 solution of the specific antibodies purchased from B&D Biosciences, Genscript, Invitrogen, Genzyme, IBL international, Innogenetics, or Calbiochem), and blocked. 100 µl of the plasma samples diluted with PBS in the ratio of 1:1, 1:2, 1:4, 1:8, 1:16; and 1:64 are added to each pre-coated well. The plates are incubated at room temperature for 2 h with rotation at 700 rpm. The wells are blocked with 3% bovine serum albumin in PBS overnight at 4° C. After three washes with PBS/0.1% Tween 20, 100 µl of specific antibodies of BDNF, IGF-1, TGF-beta 1, VEGF, IL-18 and MCP-1 are applied to each well, and incubated overnight at 4° C. 50 µl of HRP-linked secondary antibody, which are specific to the primary antibody, are added, and incubated at room temperature for 2 h with rotation at 700 rpm. The plate is washed three times with 0.1 M PBS (sodium bicarbonate buffer, Sigma, pH 9.6) to remove unbound antibody-enzyme conjugates. 100 µl TMB (3,3',5,5'-tetramethylbenzidine) is added, which is converted by the enzyme into a yellow color in the presence of a 3% solution of $H_2O_2$ in methanol. The reaction is stopped with the addition of 100 µl of 3 N sulfuric acid. The absorbance of the plate wells is measured at 450 nm to determine the presence and quantity of antigen. The correlation of absorbance and concentration are the standard (reference) curves for the test samples.

TABLE 5 shows the combination of the biomarker as defined herein whereby the numbering is as follows: 1 = BDNF, 2 = IGF-1, 3 = VEGF, 4 0 TGF-beta 1, 5 = MCP-1, 6 = IL-18

| Symbol | Analyte combination |
| --- | --- |
| A | 1 & 2 |
| B | 1 & 3 |
| C | 1 & 4 |
| D | 1 & 5 |
| E | 1 & 6 |
| F | 2 & 3 |
| G | 2 & 4 |
| H | 2 & 5 |
| I | 2 & & |
| J | 1 & 2 & 3 |
| K | 1 & 2 & 4 |
| L | 1 & 2 & 5 |
| M | 1 & 2 & 6 |
| N | 1 & 2 & 3 & 5 |
| O | 1 & 2 & 4 & 5 |
| P | 1 & 2 & 3 & 4 & 5 |

Example 4: Determination of Homocysteine

Homocysteine is measured by high-performance liquid chromatography (HPLC) with fluorescence detection following the procedure of Araki A. and Sako Y., J. Chromatogr. 422:43-52, 1987.

Figure 2:
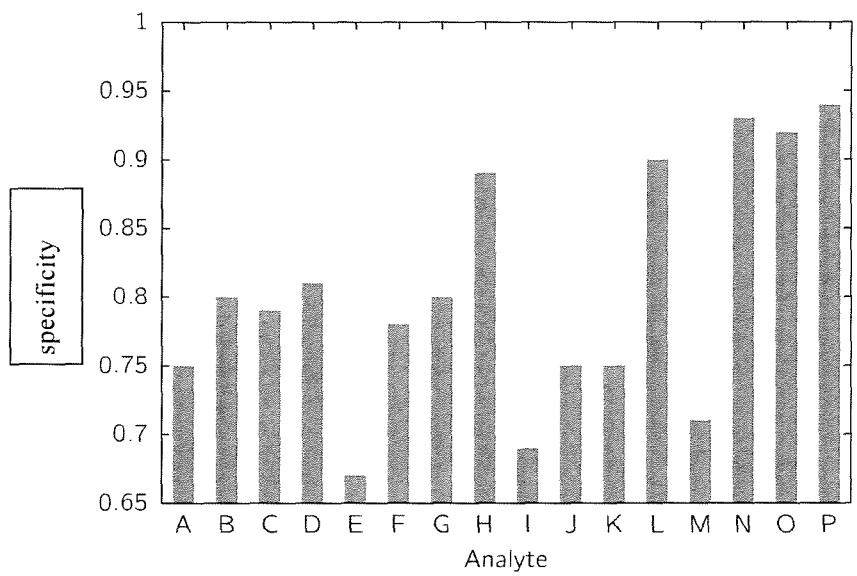
In FIG. 2, the specificity of the marker combinations shown in table 5 is shown. As demonstrated, using at least four marker out of the six marker allows a specificity of more than 90%.

Results:

In FIG. 2 the relevance of combining at least 4 out of the 6 biomarker as defined herein on the specificity is shown. As demonstrated, a specificity of at least 90% is obtained only when combining at least 4 marker which is however sufficient to obtain a specificity of at least 90%.

The invention claimed is:

1. A method of detecting elevated or decreased levels of Alzheimer's disease (AD) biomarkers in a biological sample obtained from a subject suspected of having AD comprising
   a) obtaining the biological sample from the subject;
   b) measuring a level or amount of the AD biomarkers in the biological sample, wherein the AD biomarkers comprise at least five biomarkers selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), wherein the AD biomarkers are in a form of a protein or peptide; and
   c) comparing the level or amount of the AD biomarkers to a reference level or amount of said biomarker derived from subjects not afflicted with AD.

2. The method according to claim 1 wherein the measuring step includes measuring a combination of the biomarkers selected from
   a) BDNF, IGF-1, VEGF, IL-18 and MCP-1;
   b) BDNF, VEGF, TGF-beta 1, IL-18 and MCP-1;
   c) IGF-1, VEGF, TGF-beta 1, IL-18, MCP-1; or
   d) BDNF, IGF-1, VEGF, TGF-beta 1, MCP-1,
   wherein each of a)-d) is measured along with at least one other biomarker of said at least five biomarkers.

3. The method according to claim 1 wherein the biological sample is selected from tissue or body fluid.

4. The method according to claim 1 wherein the measuring step is performed using one or more of an immunoassay selected from the group consisting of an ELISA, RIA, multiplex immunoassay or immunofluorescence assay, western blot, line assay, and dot blot assay.

5. The method according to claim 1 wherein the measuring step is performed using antibodies directed specifically to the at least five biomarkers.

6. The method according to claim 1 wherein the biological sample is blood or blood serum.

\* \* \* \* \*